United States Patent [19]

Wilson et al.

[11] Patent Number: 5,536,505

[45] Date of Patent: Jul. 16, 1996

[54] CONTROLLED RELEASE MATRIX SYSTEM USING CELLULOSE ACETATE/POLY-2-ETHYL-2-OXAZOLINE BLENDS

[75] Inventors: Alan K. Wilson; Jessica Posey-Dowty, both of Kingsport, Tenn.; Stephen S. Kelley, Evergreen, Colo.

[73] Assignee: Eastman Chemical Company, Kingsport, Tenn.

[21] Appl. No.: 167,520

[22] Filed: Dec. 15, 1993

[51] Int. Cl.⁶ .................... A61K 9/22; A61K 9/70; A61K 47/34; A61K 47/38; A61K 9/14; A01N 25/10; A01N 25/12; A01N 25/34

[52] U.S. Cl. .................... 424/486; 424/488; 424/499; 424/501; 424/468; 424/408; 424/409; 424/443; 428/402

[58] Field of Search .................... 424/486, 489, 424/501, 468, 488; 428/402

[56] References Cited

U.S. PATENT DOCUMENTS

| | | | |
|---|---|---|---|
| 3,847,822 | 11/1974 | Shuey | 210/500 |
| 4,661,211 | 4/1987 | Petty-Weeks | 204/1 |
| 4,666,706 | 5/1987 | Farquharson et al. | 424/78.3 |
| 4,743,248 | 5/1988 | Bartoo et al. | 604/892.1 |
| 4,771,089 | 9/1988 | Ofstead | 524/41 |
| 4,795,641 | 1/1989 | Kashdan | 424/438 |
| 4,824,640 | 4/1989 | Hildenbrand et al. | 422/56 |
| 4,837,005 | 6/1989 | Brode, II et al. | 424/47 |
| 4,859,719 | 8/1989 | Ofstead | 523/108 |
| 4,891,230 | 1/1990 | Geoghegan et al. | 424/461 |
| 4,917,899 | 4/1990 | Geoghegan et al. | 424/461 |
| 4,921,695 | 5/1990 | Babaian et al. | 424/81 |
| 4,933,182 | 6/1990 | Higashi et al. | 424/435 |
| 4,954,381 | 9/1990 | Cabasso et al. | 428/116 |
| 4,981,874 | 1/1991 | Latter et al. | 514/682 |
| 4,990,339 | 2/1991 | Scholl et al. | 424/443 |
| 4,997,599 | 3/1991 | Steiner et al. | 424/461 |
| 5,001,009 | 3/1991 | Whitbourne | 428/412 |
| 5,019,998 | 4/1991 | Cowan et al. | 364/496 |
| 5,039,689 | 8/1991 | Daluge | 514/359 |
| 5,047,244 | 9/1991 | Sanvordeker et al. | 424/435 |
| 5,075,114 | 12/1991 | Roche | 424/470 |
| 5,102,666 | 4/1992 | Acharya | 424/487 |
| 5,120,548 | 6/1992 | McClelland et al. | 424/473 |
| 5,128,139 | 7/1992 | Brown et al. | 424/450 |
| 5,160,745 | 11/1992 | DeLuca et al. | 424/487 |
| 5,165,937 | 11/1992 | Santus et al. | 424/468 |
| 5,176,915 | 1/1993 | Hoffmann | 424/445 |
| 5,178,867 | 1/1993 | Guittard et al. | 424/473 |
| 5,206,268 | 4/1993 | Latter et al. | 514/548 |
| 5,225,184 | 7/1993 | Latter et al. | 424/45 |

FOREIGN PATENT DOCUMENTS

| | | | |
|---|---|---|---|
| 0320097 | 10/1988 | European Pat. Off. | A61K 31/55 |
| 0317274 | 11/1988 | European Pat. Off. | A61K 9/20 |
| 0335560 | 3/1989 | European Pat. Off. | A61K 9/32 |
| 0371636 | 6/1990 | European Pat. Off. | B01J 20/32 |
| 0438249A1 | 7/1991 | European Pat. Off. | A61K 31/19 |
| 0473431A1 | 8/1991 | European Pat. Off. | A61K 9/50 |
| 0453001 | 10/1991 | European Pat. Off. | A61K 9/24 |
| 0458751 | 11/1991 | European Pat. Off. | A61K 31/195 |
| 2218994 | 5/1988 | United Kingdom | C08J 3/00 |
| 2218905 | 11/1989 | United Kingdom | A61K 9/22 |
| 90/06107 | 6/1990 | WIPO | A61K 9/20 |
| 92/11845 | 7/1992 | WIPO | A61K 9/28 |
| 93/07859 | 4/1993 | WIPO | A61K 9/16 |

OTHER PUBLICATIONS

Derwent Abstract, JP58093733, Jun. 1983.

*Primary Examiner*—Edward J. Webman
*Attorney, Agent, or Firm*—Betty J. Boshears; Harry J. Gwinnell

[57] ABSTRACT

This invention relates to a controlled release matrix system comprising a homogenous mixture of poly-2-ethyl-2-oxazoline, cellulose acetate having a degree of substitution for acetyl of from about 0.5 to 3.0, and a water-soluble active ingredient.

26 Claims, 2 Drawing Sheets

EXTRACTION OF DEXTROMETHORPHAN HYDROBROMIDE FROM FILMS OF
80/20 CA/POLY-2-ETHYL-2-OXAZOLINE WITH pH 4.8 BUFFER

EXTRACTION OF DEXTROMETHORPHAN HYDROBROMIDE FROM FILMS OF
50/50 CA/POLY-2-ETHYL-2-OXAZOLINE WITH pH 4.8 BUFFER

CONTROLLED RELEASE MATRIX SYSTEM USING CELLULOSE ACETATE/POLY-2-ETHYL-2-OXAZOLINE BLENDS

FIELD OF THE INVENTION

This invention relates to the use of cellulose acetate and poly-2-ethyl-2-oxazoline (PEO) for controlled release applications using a controlled release matrix system which is activated by water.

BACKGROUND OF THE INVENTION

The area of polymer blends has been the subject of increasing interest because of the ability to tailor the properties of the resulting blend based on the properties of the starting polymers. Cellulose acetate polymers are generally not compatible (yield clear films with a single glass transition temperature) with other polymers. One area of particular interest is in the preparation of solid, homogenous water insoluble polymer/water soluble polymer miscible blends for controlled release applications. The combination of a water insoluble polymer and a water soluble polymer in a miscible blend imparts unique swelling properties to the blend. The extent of swelling is controlled by the type and amount of the water soluble components (polymer and additives) and not exclusively by the pH of the solution.

Prior work on mixtures of cellulose acetate and polyvinylpyrrolidinone (PVP) includes U.S. Pat. No. 4,743,248 which discloses osmotic pump type tablets comprised of sequential layers of a pH sensitive water soluble polymer (such as PVP) and insoluble polymers (such as cellulose acetate). The device disclosed in the above employs a very small hole which is used to release the active ingredient.

U.S. Pat. No. 4,771,089 described polymer blends which absorb at least their own weight of water. The films shown in the examples were cast from N, N-dimethylacetamide which is not a very desirable solvent because of its high boiling point and the difficulty of removing all of the solvent from the film.

EP 317, 274 discloses the use of blends of cellulose esters with PVP to coat medicaments in a fluidized bed for chewable tablets. The coating serves to mask the taste of the medicament and still deliver the medicament.

U.S. Pat. No. 5,120,548 discloses a controlled release drug delivery device comprising controlled release swelling modulators with swellable polymers using pores or holes for release.

EP-A-0335560 filed on Mar. 21, 1989 discloses a controlled release pharmaceutical preparation, comprising a core containing a pharmaceutically active ingredient, and a porous film of a hydrophobic polymeric substrate or a hydrophobic polymeric substance and a hydrophilic polymeric substance, the core being coated with the porous-film.

EP-A-0473431 filed on Aug. 29, 1992 discloses a composition coated with a blend of cellulose acetate and PVP.

However, none of the references disclose a uniformly dispersed controlled release matrix system comprising a blend of cellulose acetate and PEO and an active ingredient.

SUMMARY OF THE INVENTION

The present invention relates to a controlled release matrix system comprising a homogenous mixture of poly-2-ethyl-2-oxazoline, (hereinafter referred to as "PEO"), cellulose acetate having a degree of substitution for acetyl of from about 0.5 to 3.0, and a water-soluble active ingredient.

DETAILED DESCRIPTION OF THE DRAWINGS

Figure 1:
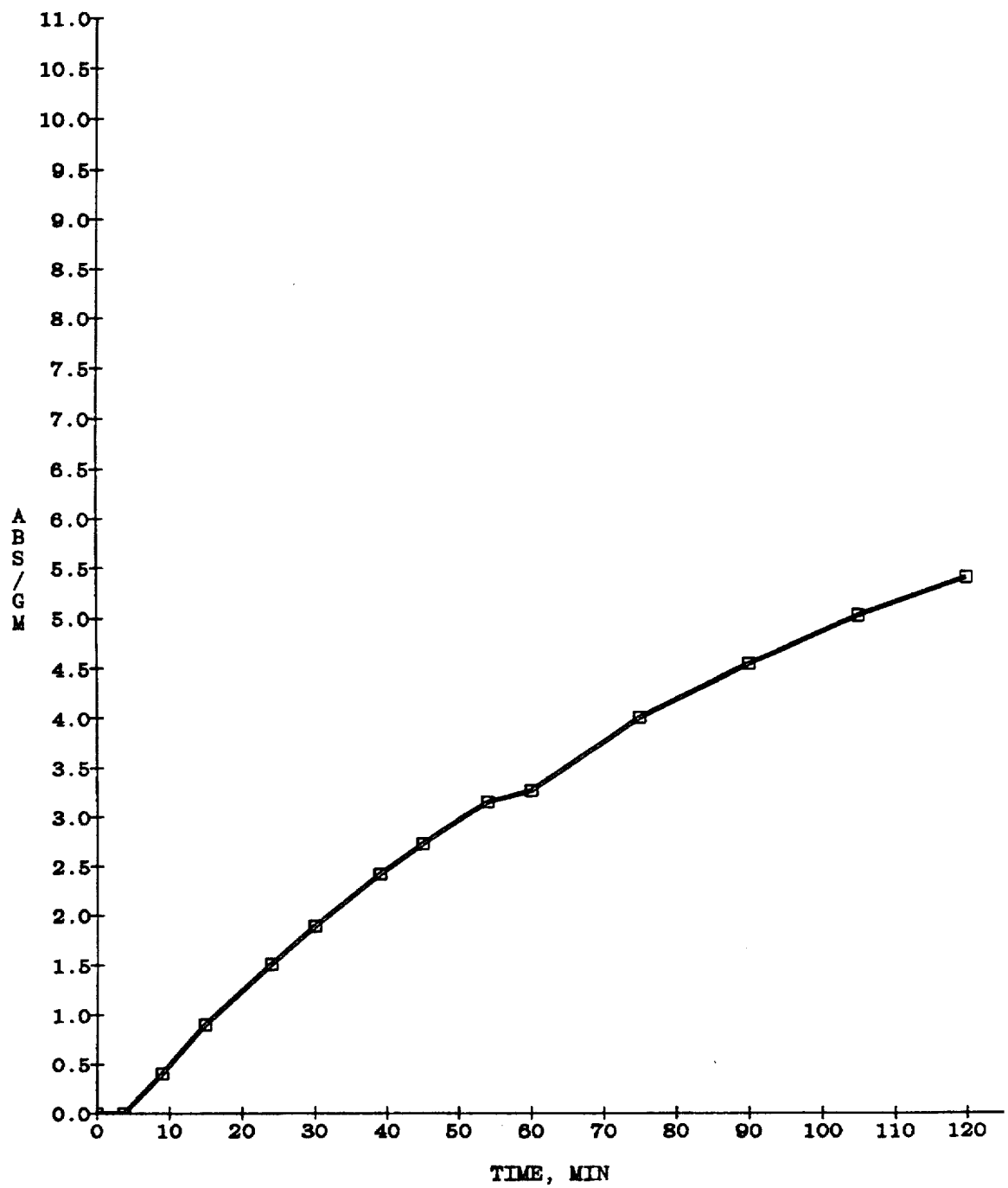
Figure 2:
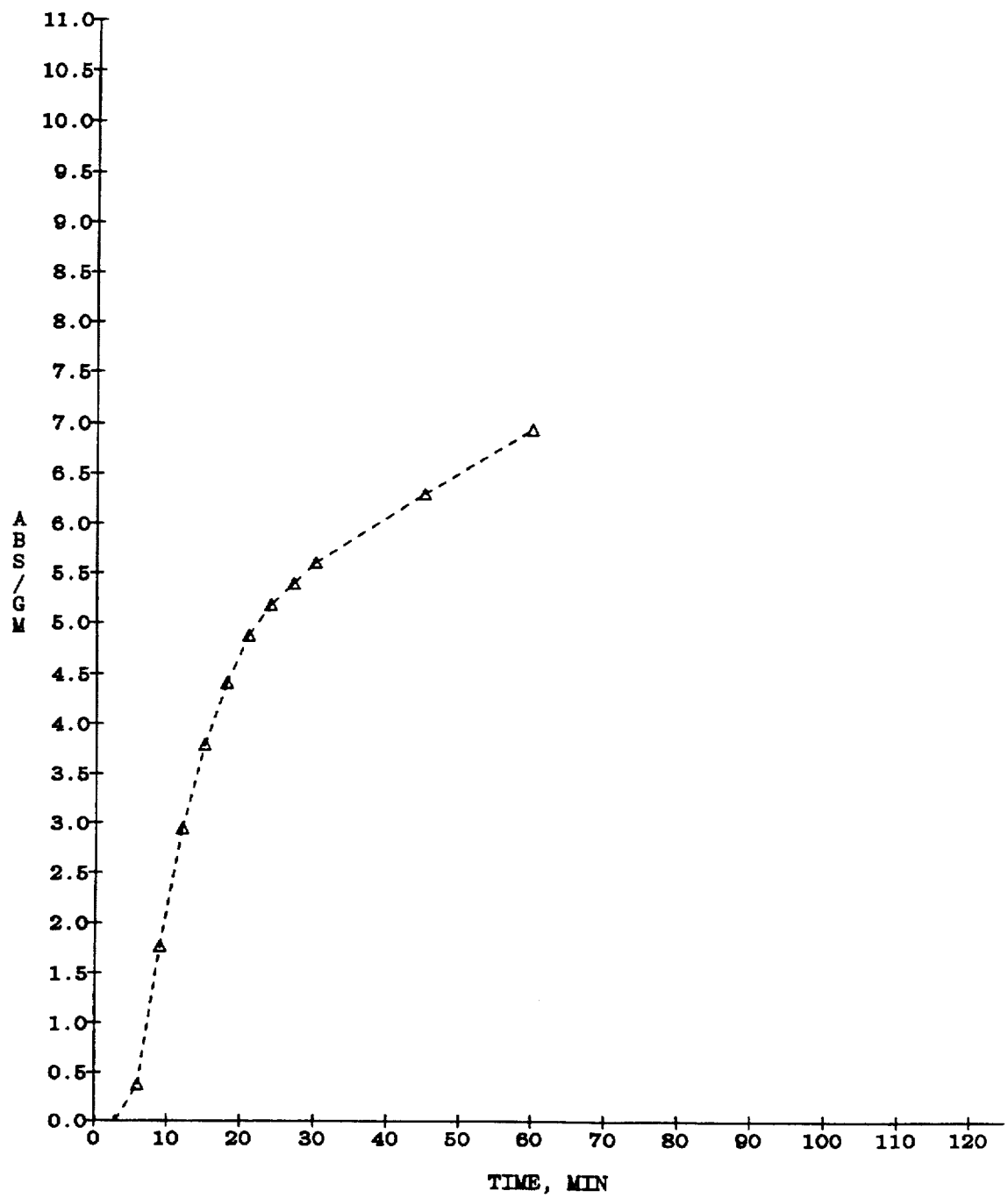

FIG. 1—graphical representation of the extraction of dextromethorphan hydrobromide measured in absorbance/gram (276.8 nanometers) from films of 2-OXAZOLINE with buffer having a pH of 4.8, FIG. 2—graphical representation of the extraction of dextromethorphan hydrobromide measured in absorbance/gram (276.8 nanometers) from films of 50/50 CA/poly-2-ethyl-2-oxazoline with buffer having a pH of 4.8.

DETAILED DESCRIPTION OF THE PREFERRED EMBODIMENTS

The present invention relates to a controlled release matrix system comprising a homogenous mixture of poly-2-ethyl-2-oxazoline (hereinafter referred to as "PEO"), cellulose acetate, (sometimes referred to as "CA"), having a degree of substitution (DS/AGU) for acetyl of from about 0.5 to 3.0, preferably about 2.0 to 2.7, and more preferably, about 2.4 to 2.55, and a water-soluble active ingredient.

For the purposes of this invention, "DS/AGU" or simply "DS" refers to the number of substituents per anhydroglucose unit where the maximum DS/AGU is three.

The poly-2-ethyl-2-oxazoline is preferably present in an amount of 5 to 80 weight %, more preferably, 15 to 50, based on the total weight of the poly-2-ethyl-2-oxazoline and cellulose acetate equalling 100 weight %.

The greater the level of poly-2-ethyl-2-oxazoline present in the blend, the greater the rate of dissolution of the active ingredient.

The cellulose acetate is preferably present in an amount of 95 to 20 weight %, preferably 85 to 50% based on the total weight for the poly-ethyl-2-oxazoline and cellulose acetate equalling 100 weight %.

The active ingredient is preferably present in an amount of 0.01 to 40 weight %, preferably, 0.5 to 20 based on the total weight of the poly-2-ethyl-2-oxazoline, cellulose acetate, and active ingredient, all components equalling 100 weight %.

The cellulose esters useful in the present invention have at least 2 anhydroglucose rings and typically have between 2 and 5,000 anhydroglucose rings; also, such polymers typically have an inherent viscosity (IV) of about 0.2 to about 3.0 deciliters/gram, preferably about 1 to about 1.5, as measured at a temperature of 25° C. for a 0.50 gram sample in 100 ml of a 60/40 by weight solution of phenol/tetrachloroethane.

The cellulose esters useful in the present invention can be prepared using techniques known in the art or are commercially available, e.g., from Eastman Chemical Products, Inc., Kingsport, Tenn., U.S.A.

The combination of the PEO and the cellulose acetate imparts unique swelling properties to the blend. The extent of swelling is controlled by the type and amount of the water soluble components and not exclusively by the pH of the solution.

The controlled release device can either be cast from solvents, extruded, injection molded, or compression molded as long as the active ingredient and water soluble polymers are stable to the conditions being used. The rate of release of the active ingredient in these systems is determined by the amount of water soluble polymer (PEO) in the system and the presence of water.

The active ingredient of the invention can be any water soluble material. However, it is preferred that the active ingredient is a pharmaceutical agent.

It is also preferred that the active pharmaceutical agent be selected from the group consisting of analgesics, anti-inflammatory agents, antibiotics, anti-depressants, anti-epileptics, anti-hypertensive agents, neuroleptics, anti-arrhythmics, corticosteroids, lipid regulating agents, antacids, laxatives, anti-ulcer agents and mixtures thereof.

It is also preferred that the active pharmaceutical agent be selected from the group consisting of dextromethorphan hydrobromide, acetaminophen, and acetylsalicylic acid.

The ratio of active pharmaceutical agent to the other components of the blends is generally from about 1:100 to 100:1 on a weight percentage basis. Preferably the ratio is from about 1:10 to about 10:1 but is governed by the type of pharmaceutical employed, its dosage, etc.

In a preferred embodiment of the invention, it is also preferred that the active ingredient be a pesticide.

The invention can also comprise other additives. Examples of these additives are fillers, lubricants, plasticizers, stabilizers and/or coloring agents.

Lubricants useful in the invention may be selected from the group consisting of stearates of aluminum, calcium, magnesium and tin as well as talc, silicones.

The lubricants are preferably present in the amount of 0.1–5 weight % based on the weight of all components of the blend.

Plasticizers useful in the invention may be selected from the group consisting of low molecular polyalkylene oxides, such as polyethylene glycols, polypropylene glycols, polyethylene-propylene glycols, organic plasticizers with low molecular weights, such as glycerol, glycerol monoacetate, glycerol, diacetate or glycerol triacetate; propylene glycol, sorbitol, sodium diethylsylfosuccinate, triethyl citrate, tributyl citrate and diethyl phthalate.

The plasticizers are preferably present in concentrations ranging from about 0.5 to 15 weight %, preferably 0.5 to 5 weight %, based on the weight of all of the components of the blend.

The invention may also comprise coloring agents. By coloring agents, we mean known azo dyes, organic or inorganic pigments, or coloring agents of natural origin.

The inorganic pigments useful in the invention may be selected from the group consisting of the oxides of iron and the oxides of titanium.

The inorganic pigments may be present in the amount of about 0.001 to 10 weight %, based on the weight of all components.

Examples of inorganic fillers useful in the invention are oxides of magnesium, aluminum, silicon, and titanium.

The inorganic fillers are preferably present in the amount of about 0.02 to 3 weight %, preferably 0.2 to 1 weight %, based on the weight of all components of the blend.

The stabilizers useful in the invention allow the blends to be thermally processed or provide storage stability, such as UV stabilizers.

The invention also involves a method for the preparation of a matrix control release vehicle comprising the step of blending into a homogeneous mixture the components of the matrix system of the invention.

The method of the invention may also involve other steps, such as compressing into tablets, pelletizing, or making into microporous film using conventional techniques known in the art.

Films containing the above components absorb water in proportion to the amount of water soluble polymer contained in the film with greater water absorption resulting from increased amounts of water soluble polymer. With repeated cycles, some of the water-soluble polymer is leached from the blend; however, the major portion of the water soluble polymer is lost from the first cycle. Correspondingly, the addition of a water soluble small molecule (as opposed to a polymer) allows the extraction by water of the small molecule at rates determined by the amount of water-soluble polymer present in the film.

The invention also relates to a novel sustained release tablet, useful in that it exhibits unexpectedly prolonged activity, a uniform dissolution rate, and formulation stability over an extended period of time which can be determined by the CA/water soluble polymer ratio.

PEO is compatible with the cellulose acetate of the invention. By compatible, it is meant that it is capable of yielding a clear film and one glass transition temperature by either differential scanning calorimetry or dynamic mechanical thermal analysis.

The components of the blends of the invention exhibit a single phase. The presence of a single phase may be indicated by several criteria such as, for example, optical clarity, a single glass transition temperature, scattering methods, ternary solution method, and so forth.

Preferably, the presence of a single phase is verified by the results of at least two tests. For example, optical clarity, as measured by transmitted light or (preferably) phase contrast microscopy, and a single value of glass transition temperature (Tg) which is distinct from the Tg of either component may be utilized. Tg may be measured by conventional methods such as standard differential thermal analysis on dried samples at a 20° C. per minute heating rate. The midpoint of the resulting transition curve is used as the Tg.

The components of the blends useful in the invention remain as a single phase, over an extended temperature range, e.g., −20° C. to 250° C., preferably including and extending beyond the extremes of the temperature range in which they will be processed, handled, and used.

It is preferred that the cellulose acetate polymer and the PEO have solubility parameters which are closely matched. Preferably, the solubility parameters of the two polymers are within 1.0 unit of each other and most preferably, within 0.5 unit of each other.

The blends useful in the invention are "miscible". As it is used herein, the phrases "miscible polymer blends" and "miscible blends" mean a composition of two or more polymer components in which the separate components are no longer separately distinguishable yet are present as individual components.

The components of the blend of the invention may be blended in an appropriate mixer at a suitable speed until a homogenous blend is obtained. For example, suitable mixers or blenders, such as planetary and high intensity mixers, are useful in thoroughly mixing the components of the blends useful in the invention. Alternatively, the components are dissolved in a suitable solvent and cast from solution. An example of a suitable solvent system is 90/10 v/v dichloromethane methanol.

As appreciated in the art, the exact components and properties of components desired for any given coating application can vary, and therefore, routine experimentation may be required to determine the optional components and proportions of components for a given application and desired properties.

Where used herein, "v/v" means volume/volume and "w/v" means weight/volume.

This invention can be further illustrated by the following examples of preferred embodiments thereof, although it will be understood that these examples are included merely for purposes of illustration and are not intended to limit the scope of the invention unless otherwise specifically indicated. The starting materials are commercially available unless otherwise noted. All percentages are by weight unless otherwise indicated.

EXAMPLES

GENERAL PROCEDURE FOR CASTING FILMS

A solution of the various polymers and additives in 90/10 v/v dichloromethane/methanol was prepared to contain 15 to 18% solids w/v. About 25 mls (about 4 gm based on solids of polymer/additive mixture) was poured onto a glass plate and covered with a 150 mm diameter Petri dish. The solvent was allowed to evaporate overnight. The resulting film was evaluated for film clarity visually. The film was further dried in a 60° C. vacuum oven overnight before further testing.

GENERAL PROCEDURE FOR WATER ABSORPTION

A strip of film was dried overnight in a 60° C. vacuum oven and accurately weighed. The film was then placed in demineralized water for 24 hours, removed, and blotted dry with facial tissue. The film was then reweighed. The percent weight gain was then calculated based on the initial and final weights. The wet film was then placed in a 60° C. vacuum oven overnight to dry. The dried film was then reweighed and the percent weight loss calculated. This constituted one cycle. The cycle was then repeated.

EXTRACTION OF DEXTROMETHORPHAN HYDROBROMIDE FROM FILMS

The following general equipment was used. A 100 ml reaction kettle with a mechanical stirrer (operated at 240 rpm) was immersed in a 37° C. oil bath. To this was added 100 ml of the appropriate solution (demineralized water or buffer). The liquid was pumped through a Perkin Elmer LC-75 Spectrophotometric Detector operating at 276.8 nM with a Beckman Model 110 A HPLC pump at 3 ml/min. and returned to the reaction kettle. The absorbance reading was read from a strip chart recording during the run. The volume of the tubing and UV cell was determined to be about 11 ml.

Films were cast from 90/10 v/v methylene chloride/ methanol containing about 10% dextromethorphan hydrobromide by weight. A 1 cm×2 cm strip was cut from the film, weighed, and placed between two wire screens. This was placed in the bottom of the reaction kettle. The agitator and HPLC pump were started. The absorbance readings were converted to absorbance/gm and plotted vs. time.

The buffer solutions used in the extraction studies were prepared as follows. For the 2.98 pH buffer 750 ml of a 0.1 N solution of potassium hydroxide solution was mixed with 3000 ml of demineralized water. Then 11.83 g of 85% phosphoric acid was added. The final pH was measured with a pH meter to be 2.98. For the pH 4.8 solution 40.83 g of potassium phosphate monobasic and 10 ml of 0.1 N potassium hydroxide were dissolved in 3000 ml of demineralized water. Finally the 7.1 pH buffer was prepared by dissolving 63.68 g of potassium phosphate tribasic and 15 ml of 85% phosphoric acid in 3000 ml demineralized water.

In the following examples, poly-2-ethyl-2-oxazoline was used as the water soluble polymer.

| Example | CA/PEO Ratio | Extraction Medium | pH | Time to Complete Release | Figure # |
|---|---|---|---|---|---|
| 1 | 80/120 | buffer | 4.80 | 95 min. | 1 |
| 2 | 50/150 | buffer | 4.80 | 95 min. | 2 |

The invention has been described in detail with particular reference to preferred embodiments thereof, but it will be understood that variations and modifications can be effected within the spirit and scope of the invention.

We claim:

1. A controlled release matrix system comprising a homogenous mixture of poly-2-ethyl-2-oxazoline and cellulose acetate having a degree of substitution for acetyl of from 0.5 to 3.0, and of a water-soluble active ingredient, wherein said cellulose acetate is present in the amount of 95 to 20 weight % and the poly-2-ethyl-2-oxazoline is present in the amount of 5 to 80 weight %, based on the total weight percentages of the poly-2-ethyl-2-oxazoline and cellulose acetate equalling 100 weight %, and wherein said active ingredient is present in the amount of 0.01 to 40 weight % based on the total weight percentages of poly-2-ethyl-2-oxazoline, cellulose acetate and active ingredient equalling 100 weight %.

2. The matrix system of claim 1 wherein said degree of substitution for acetyl is from 2.0 to 2.7.

3. The matrix system of claim 2 wherein said degree of substitution for acetyl is from 2.4 to 2.55.

4. The matrix system of claim 1 wherein said poly-2-ethyl-2-oxazoline is present in an amount of 15 to 50 weight %, and said cellulose acetate is present in an amount of 85 to 50 weight %, based the total weight percentages of said poly-2-ethyl-2-oxazoline and said cellulose acetate equalling 100 weight %.

5. The matrix system of claim 1 wherein said active ingredient is present in the amount of 0.5 to 20 weight % based on the total weight percentages of said poly-2-ethyl-2-oxazoline, cellulose acetate and active ingredient equalling 100 weight %.

6. The matrix system of claim 1 wherein said active ingredient is a pharmaceutical agent.

7. The matrix system of claim 6 wherein said pharmaceutical agent is selected from the group consisting of analgesics, anti-inflammatory agents, antibiotics, anti-depressants, anti-epileptics, anti-hypertensive agents, anti-arrhythmics, corticosteroids, lipid regulating agents, antacids, laxatives, anti-ulcer agents and mixtures thereof.

8. The matrix system of claim 7 wherein said pharmaceutical agent is selected from the group consisting of dextromethorphan, hydrobromides acetaminophen, and acetylsalicylic acid.

9. The matrix system of claim 1 wherein said active ingredient is a pesticide.

10. The matrix system of claim 1 further comprising additives.

11. The matrix system of claim 10 wherein said additives are selected from the group consisting of fillers, lubricants, stabilizers, plasticizers and coloring agents.

12. The matrix system of claim 11 wherein said lubricants are selected from the group consisting of aluminum stearate, calcium stearate, magnesium stearate, tin stearate talc, and silicones.

13. The matrix system of claim 12 wherein said lubricants are present in the amount of 0.1–5 weight %.

14. The matrix system of claim 11 wherein said plasticizers are selected from the group consisting of polyethylene glycols, polypropylene glycols, polyethylene-propylene glycols, glycerol, glycerol monoacetate, glycerol diacetate, glycerol triacetate, propylene glycol, sorbitol, sodium diethylsulfosuccinate, triethyl citrate, tributyl citrate and diethyl phthalate.

15. The matrix system of claim 14 wherein said plasticizers are present in concentrations ranging from about 0.5 to 15 weight %.

16. The matrix system of claim 15 in concentrations ranging from about 0.5 to 5 weight % based on the weight of all of the components.

17. The matrix system of claim 11 wherein said coloring agents comprise azo dyes, and organic or inorganic pigments.

18. The matrix system of claim 17 wherein said inorganic pigments are selected from the group consisting of the oxides of iron and the oxides of titanium.

19. The matrix system of claim 18 wherein said inorganic pigments are present in the amount of about 0.001 to 10 weight %, based on the weight of all components.

20. The matrix system of claim 11 wherein said fillers are inorganic and are selected from the group consisting of oxides of magnesium, aluminum, silicon, and titanium.

21. The matrix system of claim 20 wherein said inorganic fillers are present in the amount of about 0.02 to 3 weight % based on the weight of all components.

22. The matrix system of claim 21 wherein said inorganic fillers are present in the amount of about 0.2 to 1 weight % based on the weight of all components.

23. The matrix system of claim 1 compressed into tablets.

24. The matrix system of claim 1 comprising a pellet.

25. The matrix system of claim 1 made into a microporous film.

26. A method for the preparation of a matrix control release vehicle comprising the step of blending into a homogeneous mixture the components of the matrix system of claim 1.

* * * * *

UNITED STATES PATENT AND TRADEMARK OFFICE
CERTIFICATE OF CORRECTION

PATENT NO. : 5,536,505
DATED : July 16, 1996
INVENTOR(S) : Alan K. Wilson et al.

It is certified that error appears in the above-indentified patent and that said Letters Patent is hereby corrected as shown below:

Column 6, line 53 (Claim 8, line 3),

"dextromethorphan, hydrobromides" should be

--- dextromethorphan-hydrobromide, ---.

Signed and Sealed this

Twenty-second Day of October, 1996

Attest:

BRUCE LEHMAN

Attesting Officer  Commissioner of Patents and Trademarks